US00PP11139P

United States Patent [19]

Gross

[11] Patent Number: Plant 11,139

[45] Date of Patent: Nov. 30, 1999

[54] POINSETTIA PLANT NAMED 'SILVERLEAF'

[75] Inventor: Eduard Gross, Blanzac, France

[73] Assignee: Paul Ecke Ranch Inc., Encinitas, Calif.

[21] Appl. No.: 09/024,503

[22] Filed: Feb. 17, 1998

[51] Int. Cl.[6] ..... A01H 5/00

[52] U.S. Cl. ..... Plt./306

[58] Field of Search ..... Plt./306

*Primary Examiner*—Howard J. Locker
*Assistant Examiner*—Kent L. Bell
*Attorney, Agent, or Firm*—Arnold White & Durkee

[57] ABSTRACT

Poinsettia 'Silverleaf' is a new cultivar, distinguished by variegated silver/green and white foliage, pink flower bracts, compact bouquet-like growth habit and self-branching characteristics. 'Silverleaf' is a naturally occurring sport of the red bracted 'Peterstar' (U.S. Plant Pat. No. 8,259) with the same flowering response and cultural requirements. The new plant produces an interesting flowering pot plant. The new plant is resistant to epinasty after being confined to shipping containers. The post-production foliage and bract retention is good.

2 Drawing Sheets

BACKGROUND OF THE PLANT

This new poinsettia cultivar originated as a naturally occurring sport of 'Peterstar' (U.S. Plant Pat. No. 8,259) in my greenhouse in Blanzac, France in 1995. It was selected, because of its variegated silver/green and white leaves and pink flower bract color. Branching is very prolific and it has a unique bouquet-like growth habit. After selection, 'Silverleaf' was vegetatively reproduced from stem cuttings for test purposes in Encinitas, Calif. By subjecting clones of this plant to successive generations of vegetative propagation, it was demonstrated that the distinctive characteristics of 'Silverleaf' held true from generation to generation. Grown under the same greenhouse environment, 'Silverleaf' had a more compact growth habit but a similar flowering response time compared to the parent plant 'Peterstar'.

BRIEF DESCRIPTION OF THE PHOTOGRAPHS

Poinsettia 'Silverleaf' is illustrated in the accompanying color photographs.

DESCRIPTION OF THE PLANT

Figure 1:
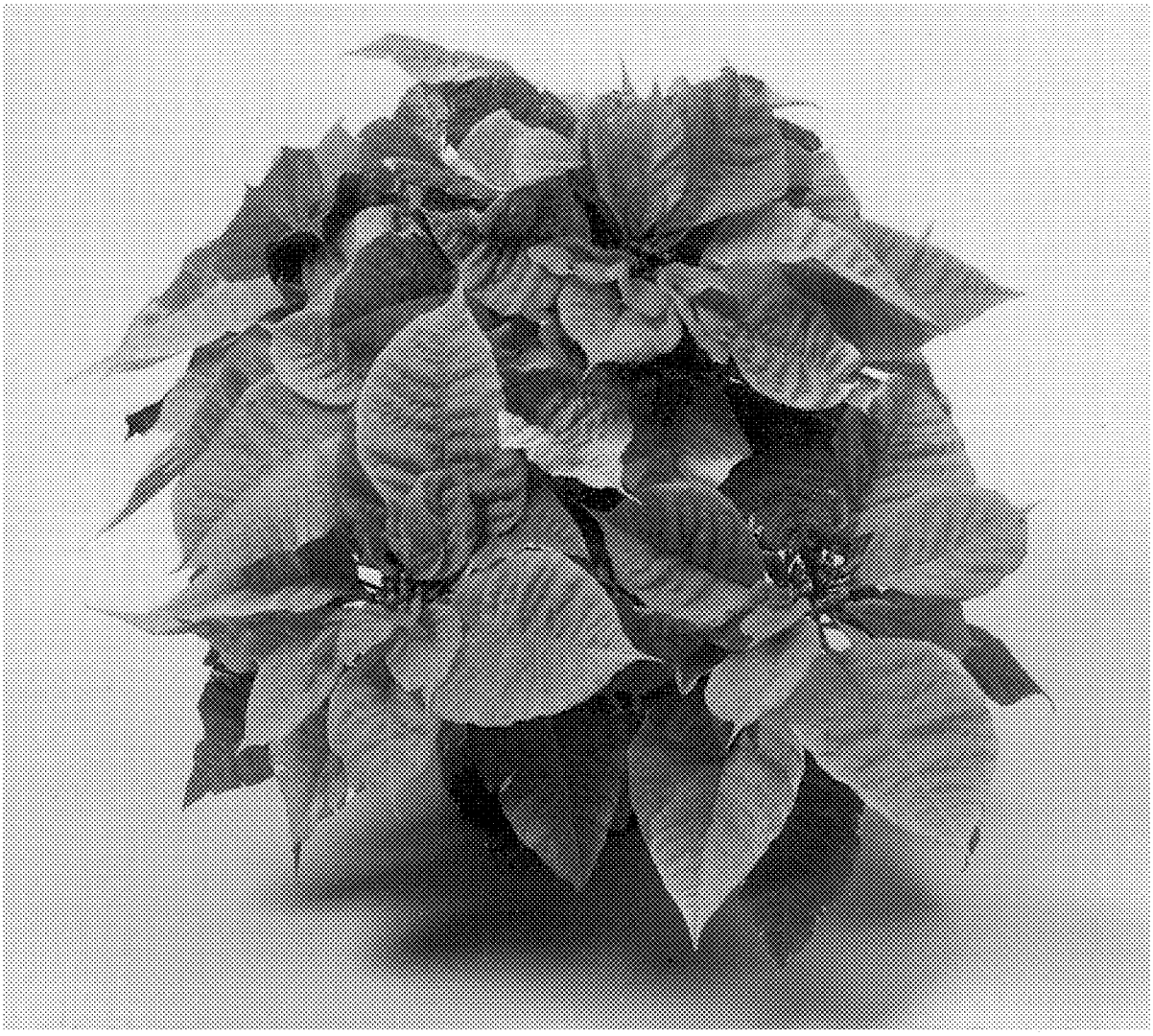
FIG. 1 is a side view of one branched plant per pot in full bloom.
Figure 2:
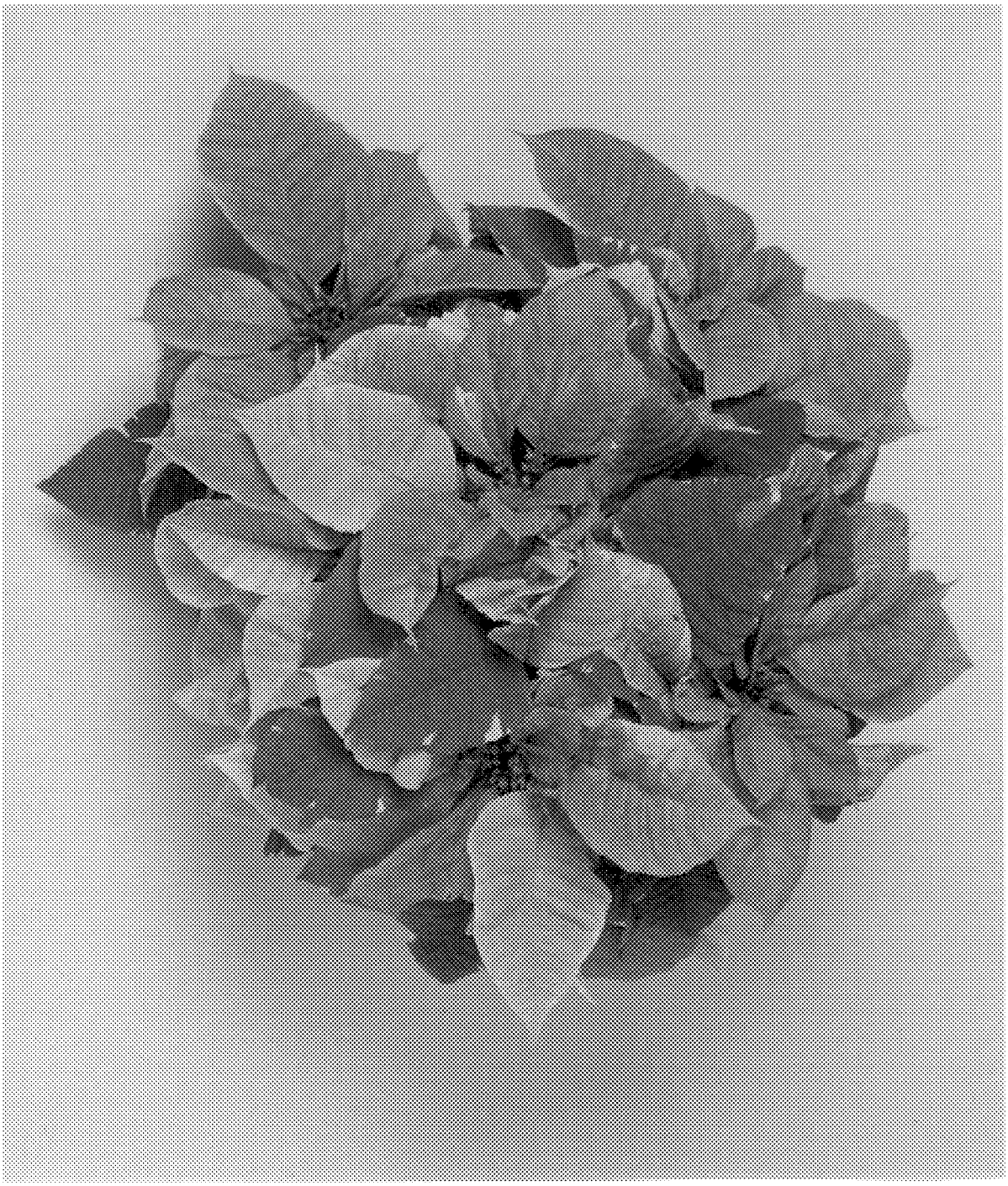
FIG. 2 is a top view of the same plant showing details of the variegated foliage, flower and bract formation.

The following is a detailed description of this new poinsettia as observed in Encinitas, Calif., USA during December 1996. Observations were recorded from flowering plants, grown as one branched plant per pot. The pot was 14 cm in diameter and 11 cm in height. Color designations are compared to the 1996 edition of R.H.S. Colour Chart, first published in 1966 by The Royal Horticultural Society, London, England.

THE PLANT

Origin: Naturally occurring sport of 'Peterstar' (U.S. Plant Pat. No. 8,259).

Classification:

*Botanical.*—*Euphorbia pulcherrima* Willd.

*Common name.*—Poinsettia.

*Cultivar name.*—'Silverleaf'.

Form: Shrub.

Height: Short.

Growth habit: As a single stemmed plant, short and compact with many self-branching side shoots. The application of a chemical growth retardant is not needed to restrict height for commercial pot plant production. I observed one branched plant in a pot with an overall height of 33 cm and an overall width of 36 cm. The diameter of individual inflorescences in 18 cm.

Branching: Axillary branches will develop and terminate in an inflorescence without pinching. However, it is usually desirable to pinch 'Silverleaf' before flower induction and remove all terminal dominance. Then, all axillary branches will develop uniformly and at a faster rate.

Growth rate: Rooting of stem cutting occurs in 12–18 days under intermittent mist.

Flowering: The plant will flower in eight to nine weeks under continuous long night conditions and night temperatures of 16–18° C. Like its parent, ('Peterstar'), 'Silverleaf' will be in full bloom in late November in the Northern Hemisphere under natural daylength conditions.

Foilage: The foliage is clean and variegated from bottom to top of the plant. The leaves are small, leaf blades typically being 10–12 cm long and 7–8 cm wide with pink petioles about 5 cm long.

*Leaf shape.*—Typical leaves are ovate with acute bases and acuminate tips. Leaf margins are mostly entire. An occasional lower leaf is modestly lobed on one side of the leaf blade.

*Leaf surface.*—The upper surface is rugose and slightly pubescent. The under surface is finely pubescent.

*Color.*—Upper side — Variegated, predominately green near R.H.S. 147B, with irregular areas of silver/green near R.H.S. 147D and irregular white wedge shaped areas along the leaf margins near R.H.S. 157D. Under side—Silver/green, near R.H.S. 147D.

*Retention.*—The foliage retention is good even under low light intensities in the consumers home Bracts: Generally there are 25–30 pink bracts of various sizes subtending the cyathia. The primary bracts have blades typically 10 cm long and 7 cm wide with pink petioles 2 cm long.

*Shape.*—Primary bracts are ovate with acute bases and acuminate tips. Leaf margins are entire. Secondary bracts are broadly elliptic to slightly obovate and have entire margins.

*Surface.*—The bract surface is rugose.

*Color.*—Upper side — Larger transitional bracts, pink, near R.H.S. 48A. Smaller bracts, dark pink, near R.H.S. 47A-B. Under side—Pink, near R.H.S. 48B.

Flowers: Generally, 20–22 cyathia (flowers) per inflorescence are present when the plant is in full bloom. Each cyathium is about 6 mm long and 6 mm wide, green in color, and fringed pink at the distal end. One or occasionally two light yellow, tinged with pink nectar cups protrude from the side of each cyathium. The flower pedicel is also green and about 5 mm in length. No stamens are present. Stigmas are pink and trifurcate. Cyathia retention is about three weeks beyond the time the flower is fully mature.

*Nectar exudate.*—None.

*Seeds.*—None.

*Fertility.*—Sterile flowers.

Post production: 'Silverleaf' is reisitant to epinasty after being confined to shipping containers. The foliage and bract retention is good, both lasting about 3 weeks.

Disease resistance: Typical of the species.

What is claimed is:

1. A new and distinct Poinsettia plant, substantially as herein shown and described, distinguished by its variegated silver/green and white foliage, pink flower bracts, compact bouquet-like growth habit, self branching and good leaf and bract retention in the consumer environment.

* * * * *